United States Patent [19]

Giaever

[11] 4,115,535

[45] Sep. 19, 1978

[54] DIAGNOSTIC METHOD EMPLOYING A MIXTURE OF NORMALLY SEPARABLE PROTEIN-COATED PARTICLES

[75] Inventor: Ivar Giaever, Schenectady, N.Y.

[73] Assignee: General Electric Company, Schenectady, N.Y.

[21] Appl. No.: 809,005

[22] Filed: Jun. 22, 1977

[51] Int. Cl.² ............................................ G01N 33/16
[52] U.S. Cl. ..................................... 424/1; 23/230 B; 424/12
[58] Field of Search .............................. 424/1, 1.5, 12; 23/230 B

[56] References Cited

U.S. PATENT DOCUMENTS

| 3,853,987 | 12/1974 | Dreyer | 424/1 |
| 3,933,997 | 1/1976 | Hersh et al. | 424/1 |
| 4,018,886 | 4/1977 | Giaever | 424/12 |

Primary Examiner—Benjamin R. Padgett
Assistant Examiner—Christine M. Nucker
Attorney, Agent, or Firm—Leo I. MaLossi; Joseph T. Cohen; Charles T. Watts

[57] ABSTRACT

A mixture of two different kinds of particles having distinctive, different properties is employed for determining the presence of a select protein in, or the absence of a select protein from, a solution. The first kind of particle provides a property facilitating separation, while the second kind of particle provides a property facilitating detection. The particles are coated with the same protein, a protein able to interact specifically with the select protein.

19 Claims, 2 Drawing Figures

DIAGNOSTIC METHOD EMPLOYING A MIXTURE OF NORMALLY SEPARABLE PROTEIN-COATED PARTICLES

BACKGROUND OF THE INVENTION

This invention relates to the detection of proteins by the utilization of the phenomenon by which such proteins interact specifically either immunologically or non-immunologically.

The use of small magnetic particles coated with a protein that will interact specifically with a select protein in order to separate such select protein from a solution is disclosed in U.S. Pat. No. 4,018,886 — Giaever. Also, the use of small magnetic particles coated with an antibody layer for sorting out and separating select viruses, bacteria and other cells from multi-cell, bacteria or virus populations is disclosed in U.S. Pat. No. 3,970,518 — Giaever.

In U.S. Pat. No. 3,933,997 — Hersh et al., composites consisting of antidigoxin antibodies coupled chemically through an intermediate silane coupling agent to magnetically responsive inorganic particles are employed for the determination of the concentration of digoxin utilizing a standard digoxin assay curve. The above-noted patents are incorporated by reference.

A common test for pregnancy involves coating small polystyrene latex spheres with the enzyme, human chorionic gonadotropin (HCG). When a woman becomes pregnant the level of HCG in the urine increases significantly. This is an indirect test in which a quantity (as determined by titer by an established procedure) of antibodies to HCG is added to a sample of female urine and is allowed to incubate for from about 5 to about 10 minutes therein. Next, HCG-covered latex spheres are mixed with the urine and the mix is allowed to incubate for from about 5 to about 10 minutes. If agglutination of the spheres takes place, the urine does not contain HCG to the level establishing a pregnant condition; if the spheres remain in single suspension, HCG was present beyond that level. Potentially this is a very sensitive and simple immunological test, but it often runs into trouble because the determination as to whether the spheres have agglutinated or not requires a subjective judgment on the part of the technician.

It would be of particular advantage to provide a more objective test of this general type and, preferably, a test, which reduces the incidence of non-specific reactions by which sticking of proteins to the spheres, or particles, occurs.

DESCRIPTION OF THE INVENTION

A mixture of two different kinds of particles having distinctive, different properties is employed for determining the presence of a select protein in, or the absence of a select protein from, a solution. The first kind of particle provides a property facilitating separation from the solution, while the second kind of particle provides a property facilitating detection. The particles are coated with the same protein, a protein able to interact specifically with the select protein, and added to the solution to be tested. Separation of particle content from the solution is effected to the extent feasible by utilizing the separation property of the first kind of particle and a determination is then made either of whether the content of the separated mass of particles exhibits to a substantial extent the detectable property of the second kind of particle, or whether the entire volume of the solution has undergone an indicative change, e.g., change of color, luminescence, etc.

By way of illustration, in a direct test for rubella a mixture of finely divided magnetic particles and finely divided fluorescent particles is used, both kinds of particles being coated with the antigenic part of the rubella virus. By mixing the antigen-coated magnetic particles and antigen-coated fluorescent particles with a sample from the patient, incubating for the proper length of time, applying a magnetic field to segregate the magnetic particles and then testing the segregated particles for fluorescence, it can be determined whether or not agglutination of the magnetic and fluorescent particles has occurred. This being a direct test, the occurrence of agglutination indicates a positive test (i.e., the antibody to rubella was present). A failure to agglutinate (i.e., the fluorescent particles remained in the solution) indicates the antibody to rubella was not present.

BRIEF DESCRIPTION OF THE DRAWING

The subject matter of the instant invention for which protection is sought is presented as claims at the conclusion of the written description of the invention set forth herein. The description sets forth the manner and process of making and using the invention and the best mode contemplated therefor, and the accompanying drawing forms part of the description for schematically illustrating the practice of the invention.

The view shown in FIG. 1 shows apparatus for contacting the mixture of protein-coated particles according to this invention with a sample liquid suspected of containing the select protein.

MANNER AND PROCESS OF MAKING AND USING THE INVENTION

The apparatus and materials disclosed herein are merely exemplary and, after an understanding of the method of this invention, other embodiments may be readily devised.

Kinds of particles providing a property which facilitates separation of those particles along with any material bound thereto in any way (e.g., as the result of an immunological interaction) include, for example, magnetically responsive inorganic particles or particles which, because of their greater density, are readily separable by gravity from lighter particles. Among the kinds of particles contributing the property of detectability would, for example, be small fluorescent particles or distinctively colored small polymer particles.

Preferably the particle sizes employed for both kinds of particles will be one micron or less, but this sizing is not critical. The mix of the two kinds of particles providing separability and detectability would preferably employ equal volumes of particles, although this, again, is not a critical feature of the invention. The amount of the mixed particles (these may be dry or in solution before mixing) to be added to the volume of sample processed should be in the range of $10^7$ to $10^{10}$ particles per ml, the preferred amount being $10^9$ particles per ml of final liquid volume.

Although the process of this invention is specifically described with respect to the conduct of a direct test for rubella, the procedure is applicable to other tests both direct and indirect, for example, the tests for pregnancy or for hepatitis.

In most instances to coat the particles employed it is merely necessary to expose the requisite amounts of the kinds of particles selected (separately or as a mixture) by dispersing the particles in a liquid containing a large concentration of the protein material. A contact period of less than one hour is usually sufficient when protein concentrations upwards of 10 micrograms/ml are employed.

In those instances in which the surface properties of either or both kinds of particles are not amenable to ready direct attachment by this process, it may be necessary to couple the protein material to such particles by the use of a coupling agent as, for example, a silane as described in the aforementioned U.S. Pat. No. 3,933,997 (column 2, lines 16–21; column 3, lines 3–13).

Figure 1:
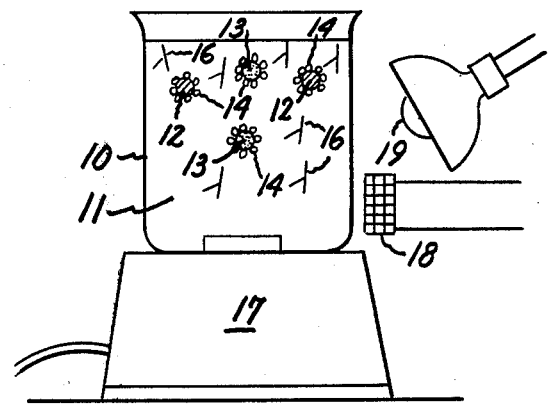
Figure 2:
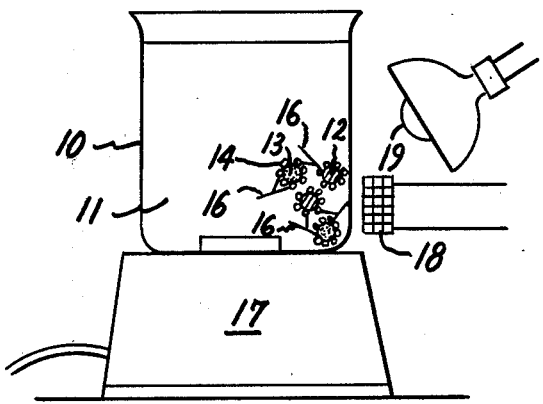
FIG. 2 shows the application of separation and detection to the system in FIG. 1.

Turning to FIGS. 1 and 2 of the drawing and describing the process of this invention in the conduct of a test for rubella virus, a beaker 10 is shown containing a sample of blood serum 11 from a patient into which antigen-coated (i.e., the antigenic part of the rubella virus) magnetic particles 12 and antigen-coated fluorescent polymer particles 13 have been introduced in the proper concentration and relative amounts.

Numerals 14 represent the coatings applied to particles 12 and 13. In the event that antibodies 16 to the rubella virus are present in the sample 11, after a proper incubation time (with or without the help of conventional stirrer 17) electromagnet 18 is actuated and, as shown in FIG. 2, the magnetic particles 12 under the influence of the magnetic field so exerted are drawn to the wall of glass beaker 10 adjacent electromagnet 11. If antibodies 16 are present, immunological reactions between antibodies 16 and antigenic coatings 14 will cause agglutination of the two kinds of spheres whereby the application of magnetic force draws not only magnetic particles 12, but also the polymer particles 13 now bound thereto by interconnecting antibodies 16.

If a significant fraction of the fluorescent plastic particles, or spheres, 13 are drawn along with the magnetic particles 12, exposure of the system to UV-light from lamp 19 will cause brighter luminescence to emanate from the region of the electromagnet 18 reflecting the presence at this location of a larger concentration of fluorescent particles. This result will indicate that the sample 11 did contain antibodies to rubella. On the other hand, if after the activation of electromagnet 18 the luminescence observed is uniform through sample 11, this will be an indication that no agglutination occurred, fluorescent particles 13 remained in solution and antibodies were absent.

The detection of the fluorescence or other detectable parameter can, of course, be measured objectively and quantitatively by the use of proper instrumentation (not shown).

Ferromagnetic, ferrimagnetic, and superparamagnetic materials are useful in the practice of this invention. Other suitable magnetic materials include oxides, such as, for example, ferrites, perovskites, chromites and magnetoplumbites. As noted hereinabove, it is preferred that the particles be about one micron or less in size.

The particles employed to contribute detectability to the system should be inert to the immunological reaction and, preferably, be relatively uniform in size. Small polymer particles in the desired size range (about one micron or less in size) may be manufactured by emulsion polymerization. For example, both acrylic and styrene-based polymer spheres have been prepared by this method. Also, according to the teachings in U.S. Pat. No. 3,257,330 — Burzynski et al., one micron organopolysiloxane beads colored and/or exhibiting fluorescence can be prepared. Polystyrene spheres ranging in size from 0.08 microns to 90 microns are commercially available from Dow Chemical Company, Midland, Michigan. These spheres are available in a variety of colors, white, pink, yellow, red, blue and green. Fluorescent polystyrene beads containing anthracene or fluorescein are also commercially available from this same source.

Among the useful combination of kinds of particles for the practice of this invention are nickel particles together with fluorescent polystyrene particles; particles of any selected metal together with polystyrene spheres in any of the colors noted hereinabove; magnetic particles together with polystyrene spheres which have been provided with radioactive tags, or particles of any metal together with polystyrene spheres that have been provided with radioactive tags. In those instances in which non-magnetic magnetic metal particles are employed, reliance is placed upon the difference in density in order to provide for particle separation under the force of gravity.

The tagging of particles (either fluorescent tags or radioactive tags is described in U.S. Pat. No. 4,011,308 — Giaever, incorporated herein by reference.

BEST MODE CONTEMPLATED

The best mode for conduct of this invention utilizes nickel particles and fluorescent polystyrene particles, both kinds of particles being about one micron or less in size and being used in about equal volumes. The concentration of the total particle content will be about $10^9$ particles per milliliter of final liquid (sample) volume.

In the conduct of the pregnancy test according to this invention an indirect test is employed. The sample of urine from a female patient is placed in a small disposable test tube. To this sample is added a quantity of antibodies to HCG. The quantity to be used will have been determined by titration to some preset standard for the HCG content establishing that a pregnant condition exists. A period of from about 5 to 10 minutes is allowed for incubation, after which the above-described nickel/polystyrene particles coated with HCG are added to and mixed with the sample. The quantity and ultimate concentration are as stated above. Once again an incubation period of from about 5 to about 10 minutes is allowed. A magnetic field is applied to one side of the test tube causing the nickel particles to move to the wall area adjacent the applied magnetic force. The test tube is exposed to UV-light. If most of the fluorescent luminescence comes from the region of the wall area adjacent the applied magnetic force, agglutination has occurred and the test has been negative (i.e., insufficient HCG present). If the fluorescent luminescence emanates uniformly from the test tube, significant agglutination has not occurred and the test has been positive (i.e., more than enough HCG molecules are present to neutralize the antibodies).

What I claim as new and desire to secure by Letters Patent of the United States is:

1. A diagnostic method for determining the presence or absence of select protein in a liquid sample comprising the steps of:

dispersing a plurality of finely divided inert first particles and a plurality of finely divided inert second particles in the sample liquid, said first particles possessing a property facilitating separation thereof from said sample liquid, said second particles possessing a property facilitating detection thereof, said first and second particles both being coated with protein material specific to said select protein;

separating said first particles from said sample liquid utilizing the separation-facilitating property thereof, and determining whether a substantial portion of said plurality of second particles have accompanied said separated first particles.

2. The diagnostic method of claim 1 wherein said first particles are metallic and said second particles are plastic beads.

3. The diagnostic method recited in claim 2 wherein the metal particles are magnetically responsive and the plastic beads are fluorescent.

4. The diagnostic method recited in claim 3 wherein the metal particles are nickel and the fluorescent plastic beads comprise polystyrene containing anthracene.

5. The diagnostic method recited in claim 3 wherein the metal particles are nickel and the fluorescent plastic beads comprise polystyrene containing fluorescein.

6. The diagnostic method recited in claim 2 wherein the plastic beads are distinctly colored.

7. The diagnostic method recited in claim 2 wherein the plastic beads are radioactively tagged.

8. The diagnostic method recited in claim 7 wherein the metal is magnetically responsive.

9. The diagnostic method recited in claim 1 wherein the first and second particles have a size of less than about one micron.

10. The diagnostic method recited in claim 1 wherein the concentration by volume of first particles is approximately equal to the concentration by volume of the second particles.

11. The diagnostic method recited in claim 1 wherein the total concentration of said particles per milliliter of final liquid volume is in the range of from about $10^7$ to about $10^{10}$ particles/ml.

12. The diagnostic method recited in claim 11 wherein the concentration of particles per milliliter is about $10^9$ particles/ml.

13. The diagnostic method recited in claim 1 wherein the bonding of the protein material to the second particles is by means of a coupling agent.

14. The diagnostic method recited in claim 1 wherein the bonding of the protein material to the first particles is by means of a coupling agent.

15. The diagnostic method of claim 1 wherein the protein material with which the particles are coated is antigenic in nature.

16. The diagnostic method of claim 1 wherein the protein material with which the particles are coated is made up of antibodies.

17. The diagnostic method recited in claim 16 wherein the select protein is the antibody to human chorionic gonadotropin and the protein layer bonded to the particles is human chorionic gonadotropin.

18. The diagnostic method of claim 1 wherein determining whether a substantial portion of the plurality of second particles has accompanied the separated first particles is accomplished by examining said separated first particles.

19. The diagnostic method of claim 1 wherein determining whether a substantial portion of the plurality of second particles has accompanied the separated first particles is accomplished by examining the sample liquid.

* * * * *